United States Patent [19]
Kukolnikov et al.

[11] Patent Number: 5,405,382
[45] Date of Patent: Apr. 11, 1995

[54] CARDIAC VALVE PROSTHESIS

[76] Inventors: Vladimir K. Kukolnikov, ulitsa Shkolnaya, 10, kv. 68; Sergei V. Evdokimov, prospekt Rossia, 13, kv. 1; Alexandr P. Melnikov, ulitsa Sosnovaya, 22/2, kv. 54, all of Kirovo-Chepetsk, Russian Federation

[21] Appl. No.: 117,094
[22] PCT Filed: Jan. 13, 1993
[86] PCT No.: PCT/RU93/00004
 § 371 Date: Sep. 13, 1993
 § 102(e) Date: Sep. 13, 1993
[87] PCT Pub. No.: WO93/13732
 PCT Pub. Date: Jul. 22, 1993

[30] Foreign Application Priority Data

Jan. 13, 1992 [SU] U.S.S.R. .................. 5027413

[51] Int. Cl.⁶ .................. A61F 2/24; F16K 15/00
[52] U.S. Cl. .................. 623/2; 137/527
[58] Field of Search .................. 623/2, 3; 137/521, 527, 137/527.8

[56] References Cited

U.S. PATENT DOCUMENTS

| | | |
|---|---|---|
| 4,274,437 | 6/1981 | Watts . |
| 4,276,658 | 7/1981 | Hanson . |
| 4,443,894 | 4/1984 | Klawitter .................. 623/2 |
| 4,451,937 | 6/1984 | Klawitter .................. 623/2 |
| 4,488,318 | 12/1984 | Kaster .................. 623/2 |
| 4,676,789 | 6/1987 | Sorensen et al. .................. 623/2 |

FOREIGN PATENT DOCUMENTS

| | | |
|---|---|---|
| 3701704 | 8/1988 | Germany . |
| 1978851 | 12/1982 | U.S.S.R. . |
| 1540818 | 2/1990 | U.S.S.R. . |
| 90/104367 | 5/1990 | WIPO . |

*Primary Examiner*—Randall L. Green
*Assistant Examiner*—Mary Beth D. Jones
*Attorney, Agent, or Firm*—Ladas & Parry

[57] ABSTRACT

The cardiac valve prosthesis comprises a circular body (1) accomodating a locking element in the form of two folds (2) mounted pivotable in relation to the body (1). The internal surface of the body (1) is made concave and substantially spherical, while the side surface of each fold (2) is made convex and substantially spherical, the center (0) of the spherical surfaces lying on the central axis (5) of the prosthesis. The folds (2) are pivotable around an axis extending in the plane of the cross-section of the prosthesis and intersecting its central axis (5). The prosthesis is intended for use in cardiosurgery for replacement of affected natural aortic and mitral valves of the human heart.

5 Claims, 2 Drawing Sheets

CARDIAC VALVE PROSTHESIS

FIELD OF ENGINEERING

This invention relates to medical engineering and, more specifically, to a cardiac valve prosthesis.

REVIEW OF THE PRIOR ART

Known in the prior art (Ref. US, A, 4276658) is a cardiac valve prosthesis comprising a circular body accomodating a locking element made in the form of two pivotable folds, each of which has a surface facing the direct blood flow, a surface facing the reverse blood flow, and a side surface coming to contact with the internal surface of the circular valve body, as well as means for fixation of said folds inside the circular valve body, which means include recesses having a surface of revolution formed on the internal surface of the body and projections on each of said folds whose side surface reproduces that of the recesses. Said means for positioning the folds inside the circular valve body enable the folds to pivot from a valve closure position to a valve opening position and vice versa around axes extending in parallel to the plane in which lies the parting line of the folds.

However, the art-known cardiac valve prosthesis suffers from insufficient reliability, since the surface area over which said fold positioning means inside the circular valve body (recess-projection surface contact area) comes to contact is small and, as a result, the wear-out of the contacting surfaces has a localized nature and, consequently, an increased surface wear-out is possible, while great local build-ups of stress concentrations in the prosthesis material are conducive to premature failure of the cardiac valve prosthesis.

Equally known in the prior art is a cardiac valve prosthesis (Ref. US, A, 4274437) comprising a circular body accomodating a locking element realized in the form of two folds pivotably rotatable in relation to the body, each of which folds has a surface facing the direct blood flow, a surface facing the reverse blood flow, a junction surface with the second fold, and a side surface coming to contact with the internal surface of said circular valve body, as well as means for positioning said folds positioning recess inside said circular valve body. The latter comprises a recess formed all along the entire circumferential length of its internal surface, and projections formed in the form of bodies of revolution protruding from each of said folds. Said fold positioning means inside the circular valve body enable the folds to pivotably turn from a valve closure position to a valve opening position and vice versa around axes running in parallel to the plane in which the folds join one another, as well as to revolve around the central axis of the prosthesis.

Nevertheless, although the latter cardiac valve prosthesis features a better reliability, since the wear-out of the recess formed in the circular valve body as the folds revolve around the central axis of the prosthesis is uniformly distributed all along the entire circumferential length of the internal surface of the body, yet there exists a possibility for an increased local wear-out and for a collapse of the contacting surfaces of the projections on the folds coming to contact over a small contact surface area, whereby the service life of the prosthesis is shortened.

BRIEF DESCRIPTION OF THE SUBSTANCE OF THE INVENTION

The present invention seeks to solve the problem of conceiving such a cardiac valve prosthesis comprising such a folds-to-body positioning assembly in which the surface area of the contacting surfaces of the folds and body would be as large as possible, while preserving the freedom of the folds to freely revolve within the valve body, since these advantageous features would permit to prevent the formation of local wear-out zones and, consequently, to improve reliability of the cardiac valve prosthesis in operation.

The above-formulated problem is solved by using the following approach: in a cardiac valve prosthesis comprising a circular valve body accomodating a locking element realized in the form of two pivotable folds capable of rotating in relation to said valve body, each of which folds has a surface facing the direct blood flow, a surface facing the reverse blood flow, a junction surface with the second fold, and a side surface coming to contact with the internal surface of said circular valve body, there are introduced the following improvements in accordance with the present invention: the internal surface of the circular body comprises at least one portion realized in the form of a concave, substantially spherical surface; said side surface of each fold is realized in the form of a convex, substantially spherical surface; the centres of said spherical surfaces lie on the central axis of the prosthesis, said folds being arranged pivotably for rotation about an axis extending in a plane passing in the cross-section of the prosthesis and intersecting its central axis. To enable the folds to easily rotate around the central axis of the body in order to reduce the wear-out of the circular body, the latter comprises a portion realized with a concave surface extending all along the entire circumferential length of the internal surface of the valve body.

As regards cardiac valve prostheses intended to be implanted to patients affected with pathologic anomalies of the left ventricle of the heart, for which patients it is undesirable that the prosthesis folds would revolve around its central axis because of a possible resistance offered by surrounding heart components, an alternative embodiment is preferable, in which the internal surface of the circular valve body comprises two diametrically opposite portions realized with a concave, substantially spherical surface, the centres of the spherical surfaces also lying on the central axis of the prosthesis.

In order to provide optimum conditions for the blood flow distribution through the flow passage of the cardiac valve prosthesis, each of its folds is provided with at least one cam arranged on the surface facing the reverse blood flow and adapted to cooperate by its profiled portion with the corresponding portion of the cam of the other fold, and also provided with two detents arranged singly at the ends of said folds junction surface with a possibility to cooperate with the valve body from its side facing the direct blood flow in order to limit the pivotal movement of the folds.

To ensure unobstracted pivotal movement of the folds within the circular valve body, it is advisable that the radius of the sphere forming its internal surface be made greater than the radius of the spherically shaped side surface of the folds.

The cardiac valve prosthesis manufactured in accordance with the present invention features a superior reliability because of lower contact stresses arising between expanded cooperating contact surfaces of the body and the folds, and because of the fact that the wear-out zones become uniformly distributed all along the entire internal surface of the body and over the side surface of the folds.

In addition, the cardiac valve prosthesis realized in accordance with the present invention offers a number of additional advantages, such as a reduced pressure loss, a reduced blood traumatism rate and an enhanced resistance to the thrombe formation owing to the fact that the internal surface of the valve body is made smooth, without local projections nor recesses liable to cause additional disturbances in the blood flow.

BRIEF DESCRIPTION OF DRAWINGS

In what follows, the present invention is explained by the description of its specific embodiments and is illustrated by appended drawings, wherein.

Figure 1:
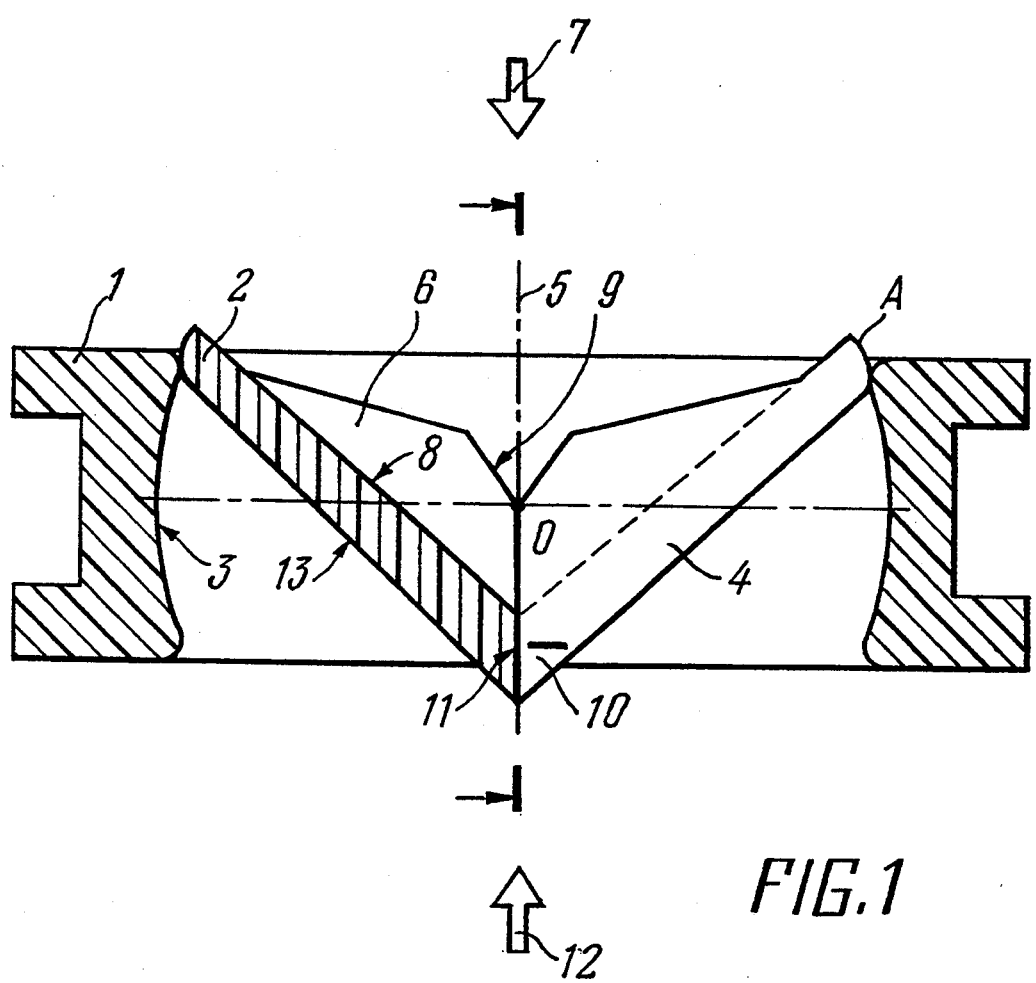
FIG. 1 represents the cardiac valve prosthesis in accordance with the present invention and provides a longitudinal sectional view of a first embodiment thereof having a single concave surface portion.

Now referring to FIG. 1, the cardiac valve prosthesis comprises a circular body 1 accomodating a locking element realized in the form of two folds which are pivotable with respect to the body 1. The internal surface 3 of the body 1 represents a concave surface all along its entire circumferential length, while the side surface 4 of each fold 2 represents a convex, in the given case, spherical surface having its centre 0 lying on the central axis-5 of the prosthesis. The folds 2 are pivotably arranged within the body 1 for rotation about an axis extending in a plane passing in the cross-section of the prosthesis and intersecting its central axis at a point 0. The height of the body 1 is selected to be such as to provide a contact of its internal surface 3 with the entire side surface 4 of the folds 2 in their closed position. Each fold 2 is provided with at least one cam 6 (in the present embodiment two cams 6) arranged on a surface 8 facing the reverse blood flow 7 (conventionally shown by an arrow) to cooperate by its profiled portions 9 with the cams 6 of the other fold 2. Detents 10 arranged at the ends of a surface 11, in which the folds 2 join each other, serve to limit the pivotal movement of the folds 2. The radius of the spherical surface 3 of the body 1 is made greater than the radius of the spherical surface 4 of the folds 2 by the value of a clearance (conventionally not shown in the drawing) left between them to ensure free rotation of the folds 2. The surface 8 of the folds 2 facing the reverse blood flow 7 and the surface 13 facing the direct blood flow 12 (shown by an arrow) may have any suitable shape, such as, e.g. they may be flat, cylindrical or spherical.

Figure 2:
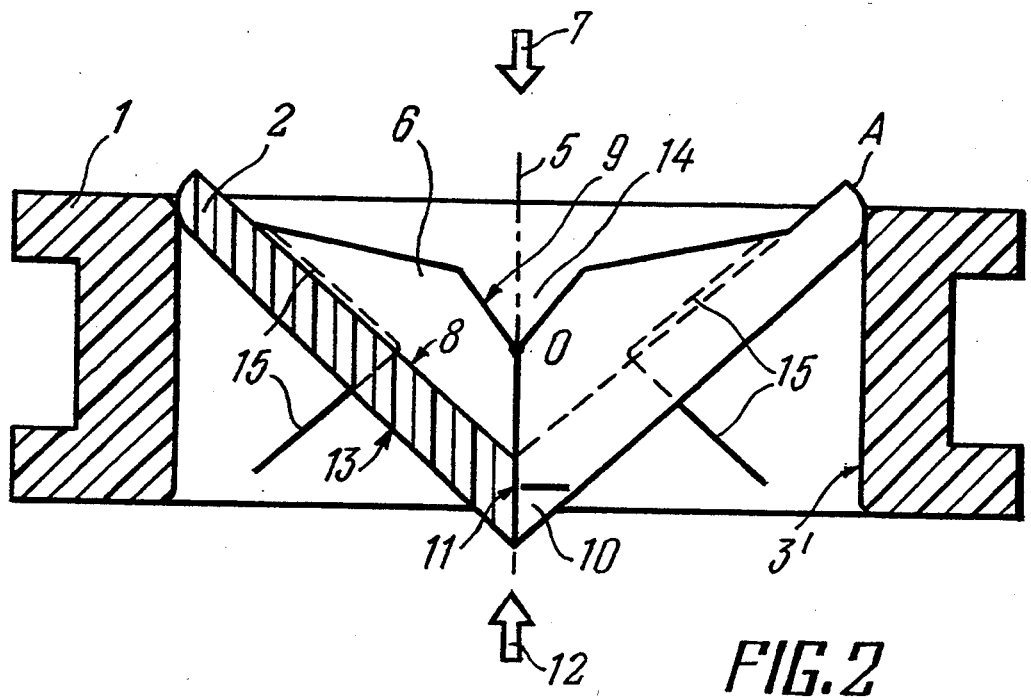
FIG. 2 is the same as in Pig. 1, a second embodiment with two concave surface portions.

The embodiment of the cardiac valve prosthesis shown in FIG. 2 differs from that of FIG. 1 in that the internal surface 3' of the circular body 1 has two diametrically opposite portions 14 in the form of a "butterfly" with an essentially concave spherical surface having its centre 0 lying on the central axis of the prosthesis, and also having edges 15 at the point of intersection with the internal surface 3' of the body 1.

Figure 3:
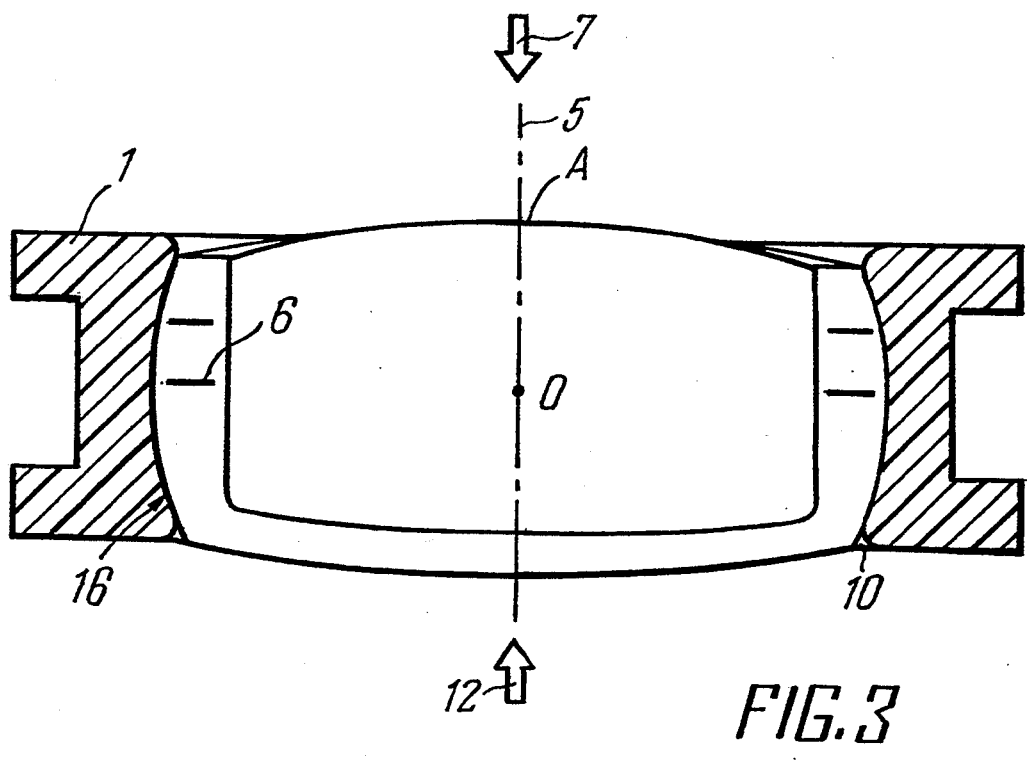
FIG. 3 is a sectional view along the line III—III of FIG. 1.

It is most advisable that the external surfaces 16 (FIG. 3) of the cams 6 be realized in such a manner that their shape would coincide with that of the side surface 4 of the folds 2, since this arrangement expands the contact surface area of the body 1 with the folds 2.

The cardiac valve prosthesis comprises, apart from the above-mentioned components, a collar for fixation of the prosthesis to the heart tissues, this collar being normally fixed on the external surface of the body (this collar is not conventionally shown in the drawings).

The Complete Specification of the present invention describes in what follows such an embodiment of the cardiac valve prosthesis in which the cooperating surfaces of the valve body and folds are realized in the form of spherically shaped surfaces, but it will be appreciated that there are possible yet other alternative embodiments of the cooperating surfaces, without, however, altering the substance of the present invention.

The cardiac valve prosthesis in accordance with the present invention is operated as follows:

As an excessive pressure is built up at the inlet of the prosthesis, the folds 2 (FIGS. 1 and 3), cooperating by their side surfaces 4 with the internal spherical surface 3 of the body 1 and with the profiled portions 9 of the cams 6, are caused to pivot about an axis intersecting the central axis 5 at a point 0 and perpendicular thereto, thereby letting to pass the direct blood flow 12 and distributing the latter into approximately three equal parts in the flow passage of the prosthesis. In so doing, the detents 10 of the folds 2 come to touch the internal surface 3 of the valve body 1 and limit the pivotal movement of the folds 2, thereby defining their opening angle, at which the surfaces 8 are aligned substantially in parallel to each other. The blood blood flow structure thus-formed ensures the minimal pressure loss in the prosthesis and a uniform irrigation of all of its surfaces with circulating blood.

As an excessive pressure is built up at the prosthesis outlet, the folds 2, cooperating by their side surfaces 4 with the internal surface 3 of the valve body 1, are caused to pivot to close the flow passage of the prosthesis. In so doing, the distal edge A may serve as the folds pivoting limiter.

A cooperation of the folds 2 side surfaces 4 with the internal surface 3 of the body 1, as the folds 2 pivot from their closure position to their opening position and vice versa, owing to the fact that they are made convex and spherically shaped all along the height of the valve body 1, this cooperation takes place over an expanded contact surface area, thereby achieving a reduction and a more uniform distribution of the contact stress concentrations, thus reducing the wear-out rate and the prosthesis components and, consequently, enhancing the operational reliability of the prosthesis.

The fact that the internal surface 3 of the valve body 1 is formed concave all along its circumferential length (in its embodiment with a single concave surface portion) enables the folds 2, in addition, to pivot around the central axis 5 during operation of the prosthesis. This arrangement makes it possible to distribute the wear-out of the internal surface 3 of the valve body 1 all along its entire circumferential length and to ensure adequate irrigation with the blood flow of all the prosthesis surfaces, thereby preventing the formation of local worn-out zones and thrombotic deposits. As a result, the dependability and thrombosis resistance of the prosthesis are improved.

The alternative embodiment of the cardiac valve prosthesis realized in accordance with FIG. 2 functions in a manner identical to that depicted in FIG. 1, with the exception of the fact that each of the folds 2 cooperates by its side surface 4 with the edges 15 of the portions 14, thereby preventing pivotal movement of the folds 2 around the central axis 5 of the prosthesis during operation of the latter. With this particular embodiment, although the wear-out of the internal surface 3 of the valve body 1 is somewhat increased as compared to the embodiment of FIG. 1, but, instead, the work space within which the prosthesis folds 2 move becomes closed, thereby ruling out any possibility for their interfering with the heart tissues surrounding the prosthesis.

INDUSTRIAL APPLICABILITY

The cardiac valve prosthesis in accordance with the present invention is intended for use in medical establishments and in cardiosurgery for replacement of affected natural aortic and mitral valves of the human heart. Not less successfully can the present invention be used for replacement of an affected tricuspid valve.

We claim:

1. A heat valve prosthesis comprising an annular valve body accommodating a locking member comprising two leaflets pivotably mounted relative to said body, each leaflet having a blood flow facing surface, a reverse blood flow facing surface, a leaflet abutting surface to abut the leaflet abutting surface of the other of said two leaflets, and a side surface contacting an interior surface of said annular valve body, said interior surface of said annular body having at least one concave portion, substantially shaped as a sphere with a center 0 lying on a center line of said prosthesis, said side surface of each leaflet being made convex, substantially as a sphere with a center 0 lying on said center line of the prosthesis, said leaflets being mounted in said body so as, to be pivotable within said annular body, around an axis extending in a cross-sectional plane of said prosthesis and intersecting said center line of the prosthesis so as to allow said side surface of the leaflet to contact said interior surface of said concave portion of the annular body.

2. The heart valve prosthesis according to claim 1, wherein said interior surface of the annular body is circular and the at least one said portion with the concave, substantially spherical, surface extends entirely over the interior surface of the annular body.

3. The heart valve prothesis according to claim 1, wherein said interior surface of the annular body has two diametrically opposite portions each with a concave, substantially spherical, surface.

4. The heart valve prosthesis according to claim 2, wherein each leaflet is provided with at least one cam arranged on the reverse blood flow facing surface, said at least one cam having a profiled portion capable of cooperating with a corresponding profiled portion of a cam provided in said second leaflet, each said leaflet also provided with two detents arranged singly at ends of said abutting surface for cooperation with the annular body on a side which faces the direct blood flow for limiting pivotal movement of the leaflets.

5. The heart valve prosthesis according to claim 1 wherein said interior surface of said spherical concave portion of the annular body has a radius which is greater than the radius of said convex side surface of the leaflet.

* * * * *